United States Patent [19]

Shih et al.

[11] Patent Number: 4,543,432
[45] Date of Patent: Sep. 24, 1985

[54] SEPARATION OF ISOPROPYL ALCOHOL FROM TERTIARY BUTYL ALCOHOL BY SELECTIVE ADSORPTION

[75] Inventors: Tsung-Shen T. Shih, Morris Plains, N.J.; Eckhard R. Becker, Yardley, Pa.

[73] Assignee: Atlantic Richfield Company, Los Angeles, Calif.

[21] Appl. No.: 258,114

[22] Filed: Apr. 27, 1981

[51] Int. Cl.[4] ............................................. C07C 29/76
[52] U.S. Cl. ..................................... 568/917; 210/690
[58] Field of Search ......................... 568/917; 210/690

[56] References Cited

U.S. PATENT DOCUMENTS 3,021,374  2/1962  Radzitzky ..................... 568/917 X
3,121,757  2/1964  Faust ............................. 210/690 X
3,868,429  2/1975  Faulkner ....................... 210/690 X
4,064,043  12/1977  Kollman .............................. 210/690
4,309,281  1/1982  Dessau ........................... 210/690 X

*Primary Examiner*—Bernard Helfin
*Attorney, Agent, or Firm*—Michael S. Jarosz

[57] ABSTRACT

The present invention provides a novel method for removing minor amounts of isopropyl alcohol from a process stream primarily comprising tertiary butyl alcohol. The separation of isopropyl alcohol from tertiary butyl alcohol is accomplished by providing an adsorbent comprising asymetric apertures greater than five angstroms in length, and less than five angstroms in width. Preferably, a carbonaceous adsorbent comprising such apertures is utilized to effect the separation of isopropyl alcohol from tertiary butyl alcohol.

1 Claim, 7 Drawing Figures

COLUMN EFFICIENCY vs PRODUCT PURITY

BREAKTHROUGH CURVES OF IPA AND IBF ON TBA REGENERATED (60°C) AMBERSORB XE-347

BREAKTHROUGH CURVES OF IPA AND IBF

SEPARATION OF ISOPROPYL ALCOHOL FROM TERTIARY BUTYL ALCOHOL BY SELECTIVE ADSORPTION

BACKGROUND

The present invention relates to the field of tertiary butyl alcohol production, and more particularly to the production of high purity tertiary butyl alcohol.

There is a commercial demand in the United States for various grades of tertiary butyl alcohol ("TBA"). Tertiary butyl alcohol with relatively high concentrations of impurities is acceptable for use as a denaturant for ethyl alcohol. Many billions of pounds of tertiary butyl alcohol are also used in gasoline blends. Tertiary butyl alcohol produced for this purpose has a typical purity of about 96%, with major impurities being isopropyl alcohol ("IPA"), isobutyl formate ("IBF"), acetone, water, methyl ethyl ketone ("MEK") and tertiary-butyl formate ("TBF"). High purity tertiary butyl alcohol is also in demand for use as a pharmaceutical and specialty solvent, and for use in the manufacture of organic peroxides. Such high purity tertiary butyl alcohol typically contains less than 0.5% impurities. At the present time, Shell Chemical Company supplies nearly the entire domestic market for high purity tertiary butyl alcohol, which is believed to be produced by the hydration of isobutylene.

It would be advantageous to provide a simple, efficient process for purifying lower grades of tertiary butyl alcohol so that they will contain less than 0.5% impurities. Many of the impurities contained in gasoline grade tertiary butyl alcohol can be separated by conventional distillation and it has been found that production run purities ranging between 99.2% and 99.6% can be obtained using such processes. The major impurity in such refined tertiary butyl alcohol is isopropyl alcohol. Since some users of high purity tertiary alcohol demand purities in excess of 99.8%, the provision of a technique for producing tertiary butyl alcohol under production conditions in such purities is in considerable demand.

Since isopropyl alcohol boils at 82.4° C. and tertiary butyl alcohol boils at 82.2°-3° C., conventional distillation is not suitable for separating these compounds. Similarly, purification of tertiary butyl alcohol to 99.8% purity is not feasible by extractive distillation with alkane solvents since it has been found that alkane solvents form a minimum boiling azeotrope with TBA.

SUMMARY OF THE INVENTION

The present invention provides a novel method for removing minor amounts of isopropyl alcohol from tertiary butyl alcohol which comprises exposing a process stream of tertiary butyl alcohol containing said isopropyl alcohol to an adsorption medium comprising asymetric apertures having lengths in excess of five, or about six, angstroms and widths of less than five, or about four, angstroms. The preferred adsorbtion medium is a carbonaceous adsorbent comprising pores within the above-defined size ranges. This method has been shown to be effective to remove small concentrations of IPA from tertiary butyl alcohol process streams.

Accordingly, a primary object of the present invention is the provision of a novel method for separating isopropyl alcohol from tertiary butyl alcohol.

A further object of the present invention is the provision of a method for purifying isopropyl alcohol-containing tertiary butyl alcohol process streams to achieve purities in excess of 99.5%.

These and other objects of the present invention will become apparent from the following, more detailed description.

DESCRIPTION OF THE PREFERRED EMBODIMENTS

Figure 1:
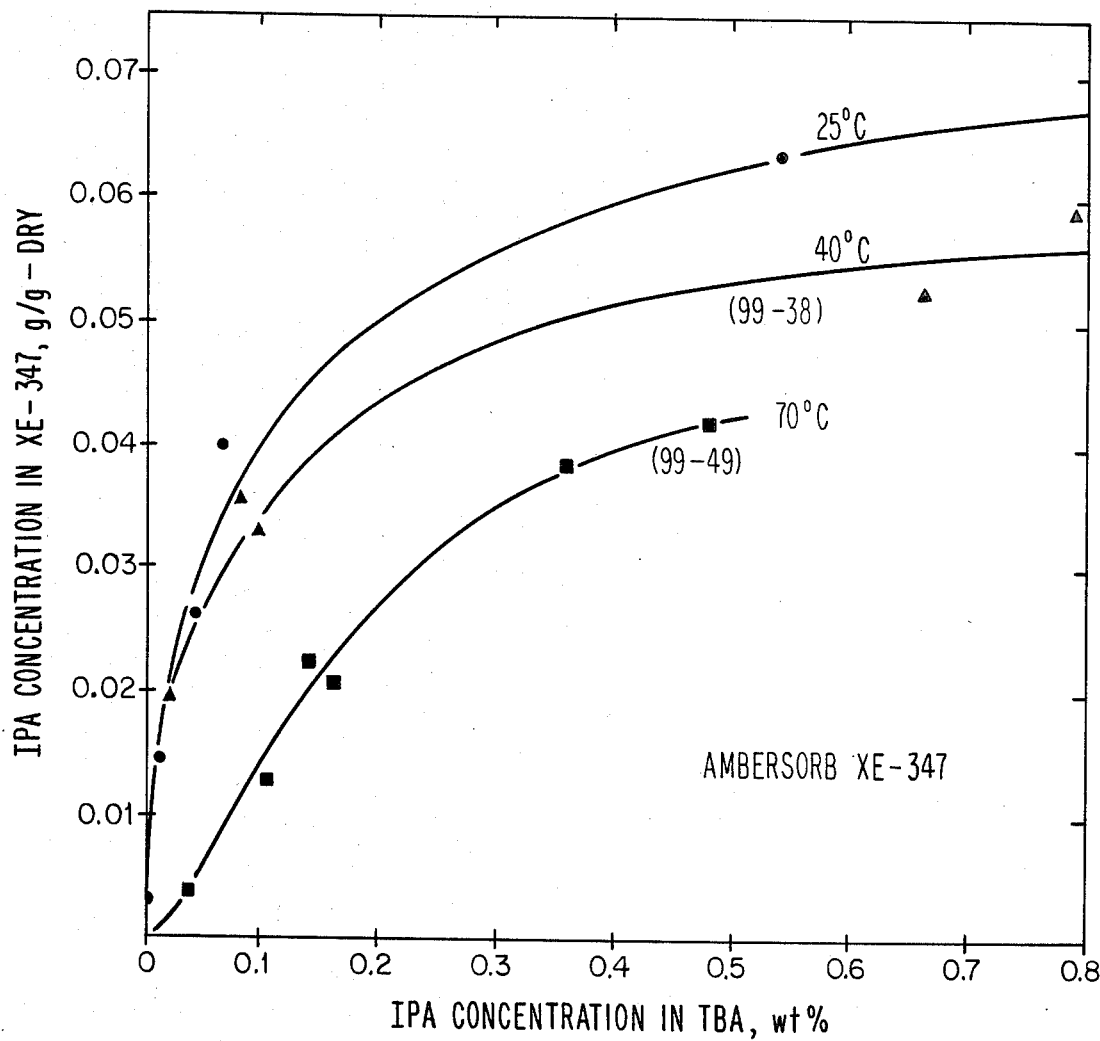
FIG. 1 is an equilibrium adsorption isotherm of isopropyl alcohol on a carbonaceous adsorbent, Ambersorb ® XE-347.

While specific examples have been selected for purposes of illustration in the following description, one of ordinary skill in the art will recognize that various departures can be made from the materials and methods described herein without departing from the scope of the present invention which is defined more particularly in the appended claims.

The present invention provides a novel method for purifying tertiary butyl alcohol process streams which contain isopropyl alcohol as an impurity. This method comprises the provision of an adsorbent material having asymetric pores of preselected sizes which are utilized selectively to adsorb isopropyl alcohol from a tertiary butyl alcohol process stream. Accordingly, the present invention provides a process wherein the equilibrium capacity of the adsorbent, and its "adsorption capacity", are important factors in determining the effectiveness of a given adsorbent to purify a given process stream.

As used herein the term "equilibrium capacity" refers to determinations made when the liquid-solid system is in equilibrium. For example, by giving isopropyl alcohol concentrations in the liquid phase, corresponding isopropyl alcohol concentrations are present in the solid phase at a constant temperature. The "equilibrium capacity" is thus the maximum capacity that an adsorbent may have for a given material at a given temperature.

As used herein the term "adsorption capacity" refers to the amount of a material, such as isopropyl alcohol, adsorbed by an adsorbent. Adsorption capacity is determined through continuous flow studies using either of two methods. One of these methods investigates "breakthrough capacity", which is the total amount of adsorbed material (IPA) before that material (IPA) can be detected in effluent samples. The second method for determining adsorption capacity is a determination of the "total capacity" wich is based upon the total amount of material (IPA) adsorbed when the effluent concentration becomes close to or the same as the influent concentration, these concentrations being based on per unit weight of dry adsorbent.

As used herein the term "column efficiency" refers to the ratio of adsorption at a constant breakthrough to the equilibrium capacity based on the influent concentration at a given temperature.

In accordance with the present invention, an adsorbent is provided which has asymetric pores wherein the pores have lengths in excess of five, preferably about six, angstroms and have widths of no more than above five, preferably four angstroms. Such pores exhibit a much greater affinity for isopropyl alcohol than for tertiary butyl alcohol, in spite of the similar molecular sizes of these compounds. The preferred adsorbent of the present invention is a carbonaceous adsorbent which meets the above-described criteria, and which is sold by the Rohm and Haas Company, Philadelphia, PA, under the trademark "Ambersorb XE-347". Ambersorb® XE-347 is an adsorbent which is described by Rohm and Haas as being a macroporous carbon molecular sieve similar to zeolites which can effect separations of mixtures by molecular size. For a further description of such adsorbents, please refer to U.S. Pat. No. 4,064,043 (Kollman) which is hereby incorporated by reference.

The pore structure of Ambersorb® XE-347 is described as being of the ideal size and shape for maximum interaction with aromatic molecules and unsaturated hydrocarbons. Rohm and Haas states:

"Although Ambersorb XE-347 is suitable for aqueous as well as vapor applications, most of the information available on this adsorbent to date relates to the removal of organics from air streams." Ambersorb® Carbonaceous Adsorbents, Technical Notes, Copyright Rohm & Haas Company, 1977.

Ambersorb XE-347 is described by its manufacturer as having a bimodal distribution of pore sizes. Half its pore volume consists of transport pores 100–300 angstroms in diameter. The other half, the micropores, are "slit-shaped" openings 4–6 angstroms wide which exhibit molecular sieve properties. The exact size and high degree of uniformity of the 4–6 angstrom slit-shaped poes is demonstrated by adsorption isotherms published by Rohm and Haas for butane, isobutane, and neopentane. Rohm and Haas stages:

"Neopentane, having a molecular diameter of 6.2 angstroms is adsorbed only on the surface of the transport pores while butane (3.8 angstroms in diameter) fills the micropores even at low relative partial pressures. Because the pores are slit-shaped the flat benzene molecule is as readily adsorbed into the micropores as butane. The micropores of Ambersorb XE-347 are therefore, capable of separating molecules by size similar to a 5 angstrom zeolite molecular sieve." Rohm and Haas Technical Notes, supra.

The physical properties of Ambersorb XE-347 are listed in Table I:

TABLE I
THE PHYSICAL PROPERTIES OF AMBERSORB® XE-347

|  | Ambersorb XE-347 |
|---|---|
| Appearance | black, spherical non-dusting |
| Total Surface Area ($N_2$, BET method), $m^2/gm$ | 350 |
| Bulk Density, lbs./cu.ft. | 43 |
| Bulk Density, $g/cm^3$ | 0.70 |
| Particle Density, $g/cm^3$ (Hg displacement) | 1.05 |
| Skeletal Density, $g/cm^3$ (He displacement) | 1.85 |
| Pore Volume, $cm^3/g$ | 0.41 |
| Particle Size (U.S. Sieve Series) | 20:50 |
| Crush Strength, Kg/Particle | >3.0 |
| Ash Content, % | <0.5 |

| Pore Size Distribution: | |
|---|---|
| Diameter Range, A | Vol. % |
| <6 | 50 |
| 6–40 | 0 |
| 40–100 | 0 |
| 100–300 | 50 |
| >300 | 0 |

The method of the present invention takes advantage of the asymetric pore configuration of certain adsorbents, such as Ambersorb® XE-347. Although it is not presently known why asymetric pores permit the entrance of isopropyl alcohol in preference to tertiary butyl alcohol, it is presently theorized that differences in molecular shape and/or adsorption kinetics leads to the affinity of the carbonaceous adsorbent for IPA. Nonetheless, equilibrium capacities for IPA using different adsorbents clearly demonstrates that the aforementioned Ambersorb® X-347 is far superior to all other adsorbents tested, even those with generally symetric pore sizes in the range of 4–5 angstroms. The results of these tests are set forth in Table II.

TABLE II
EQUILIBRIUM CAPACITY OF IPA ON ADSORBENTS AT 25° C.±

| Adsorbent | Manufacturer | Wt % IPA in Solution* | Equilibrium Capacity** mg/g-Adsorbent | Experiment Reference Number |
|---|---|---|---|---|
| Molecular Sieve | | | | |
| Type 3A | Grace | 0.31 | 0.1 | 78-133 |
| Type 4A | Grace | 0.29 | 3 | 78-133 |
| Type 5A | Grace | 0.3 | 13 | 78-133 |
| Type 13X(10A) | Grace | 0.25 | 12 | 78-133 |
| Silica Gel | | | | |
| Grade 407 | Grace | 0.3 | 2.8 | 99-24 |
| Grade 03 | Grace | 0.3 | 2.3 | 99-24 |
| Grade 40 | Grace | 0.3 | 2.9 | 99-24 |
| Grade 408 | Grace | 0.3 | 3.2 | 99-24 |
| Ambersorb® | | | | |
| XE-340 | Rohm & Haas | 0.28 | 7 | 78-135 |
| XE-347 | Rohm & Haas | 0.3 | 55 | 78-135 |
| XE-348 | Rohm & Haas | 0.3 | 8 | 78-135 |
| Amberlite® | | | | |
| XAD-4 | Rohm & Haas | 0.33 | 1.4 | 99-25 |
| XAD-7 | Rohm & Haas | 0.31 | 2.3 | 99-25 |
| XAD-8 | Rohm & Haas | 0.32 | 2.6 | 99-25 |
| Activated | | 0.23 | 1.0 | 99-95 |

TABLE II-continued
EQUILIBRIUM CAPACITY OF IPA ON ADSORBENTS AT 25° C.±

| Adsorbent | Manu-facturer | Wt % IPA in Solution* | Equilibrium Capacity** mg/g-Adsorbent | Experiment Reference Number |
|---|---|---|---|---|
| Charcoal | | | | |

±Synthetic IPA/TBA solution was used.
*Equilibrium liquid concentrations.
**Capacity of less than 10 mg/g is of no practical significance in industrial applications at this liquid concentration level.

As seen from Table II, molecular sieves type 5A and 13X have a small but not commercially significant capacities for isopropyl alcohol. The capacity of Ambersorb ® XE-347 is far greater than all other adsorbents tested.

In order to investigate the effect of temperature on adsorption on IPA, equilibrium capacities were determined experimentally at 25° C., 40° C. and 70° C. using tertiary butyl alcohol to which isopropyl alcohol was added as an impurity. The equilibrium isotherms of this system are shown in FIG. 1.

Figure 2:
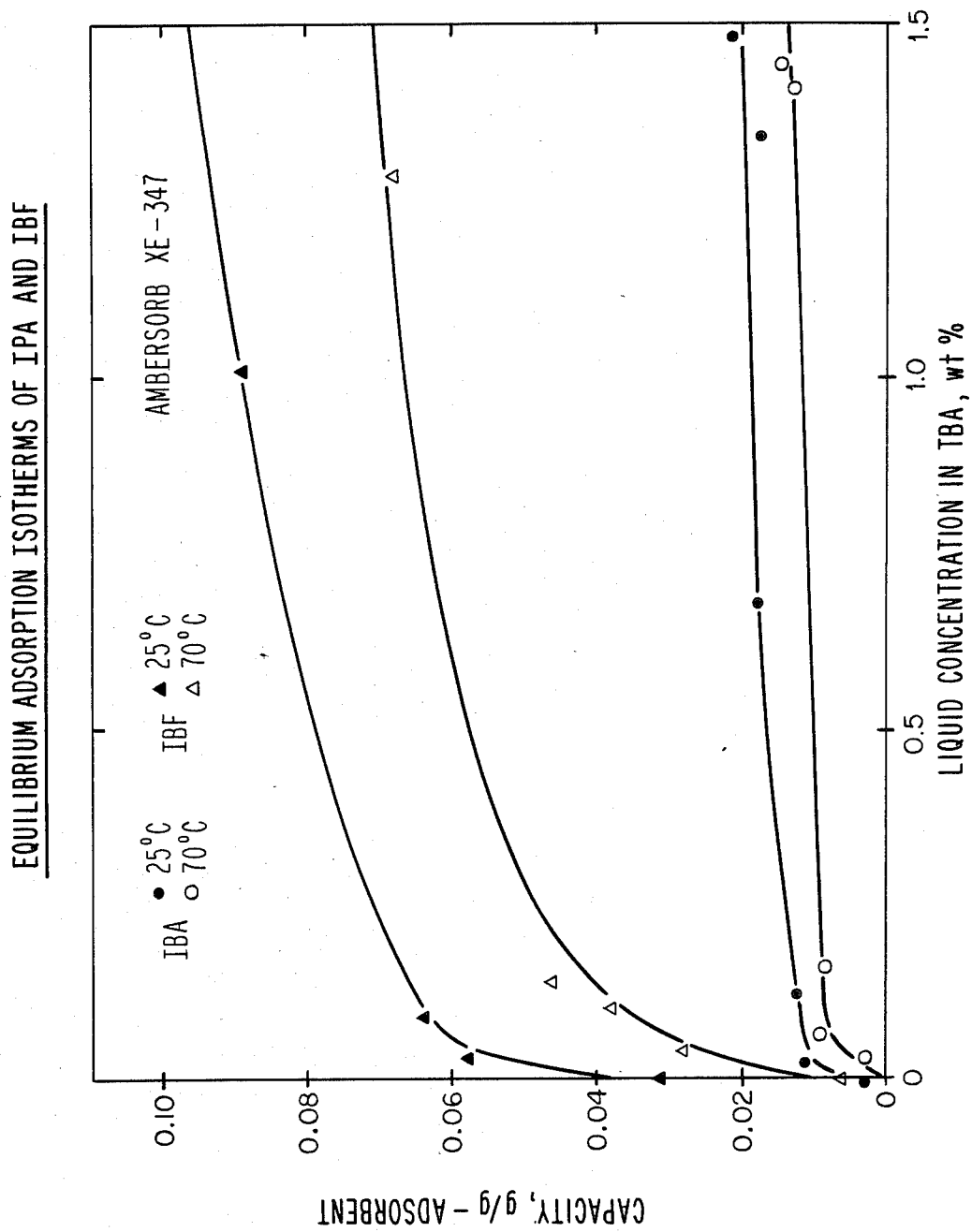
FIG. 2 is an equilibrium adsorption isotherm of isopropyl alcohol and isobutyl formate using a carbonaceous adsorbent, Ambersorb ® XE-347.

It is anticipated that the presence of other impurities in a tertiary butyl alcohol stream would undoubtedly have some effect on the capacity of isopropyl alcohol on a carbonaceous adsorbent such as Ambersorb ® XE-347. Isobutyl formate (IBF) is one impurity which may be difficult to remove completely by conventional distillation. Equilibrium experiments have shown that IBF has a great effect on the equilibrium capacity of IPA on Ambersorb ® XE-347. FIG. 2 shows the equilibrium isotherms of IPA and IBF on Ambersorb ® XE-347 at 25° C. and 70° C. IBF is chemically different from IPA and TBA and appears to have more affinity for this carbonaceous absorbent than do IPA and/or TBA. It is therefore preferred to insure that all impurities containing greater affinities for the particular carbonaceous adsorbent such as selected IBF be removed from the process stream prior to processing to remove IPA.

Figure 3:
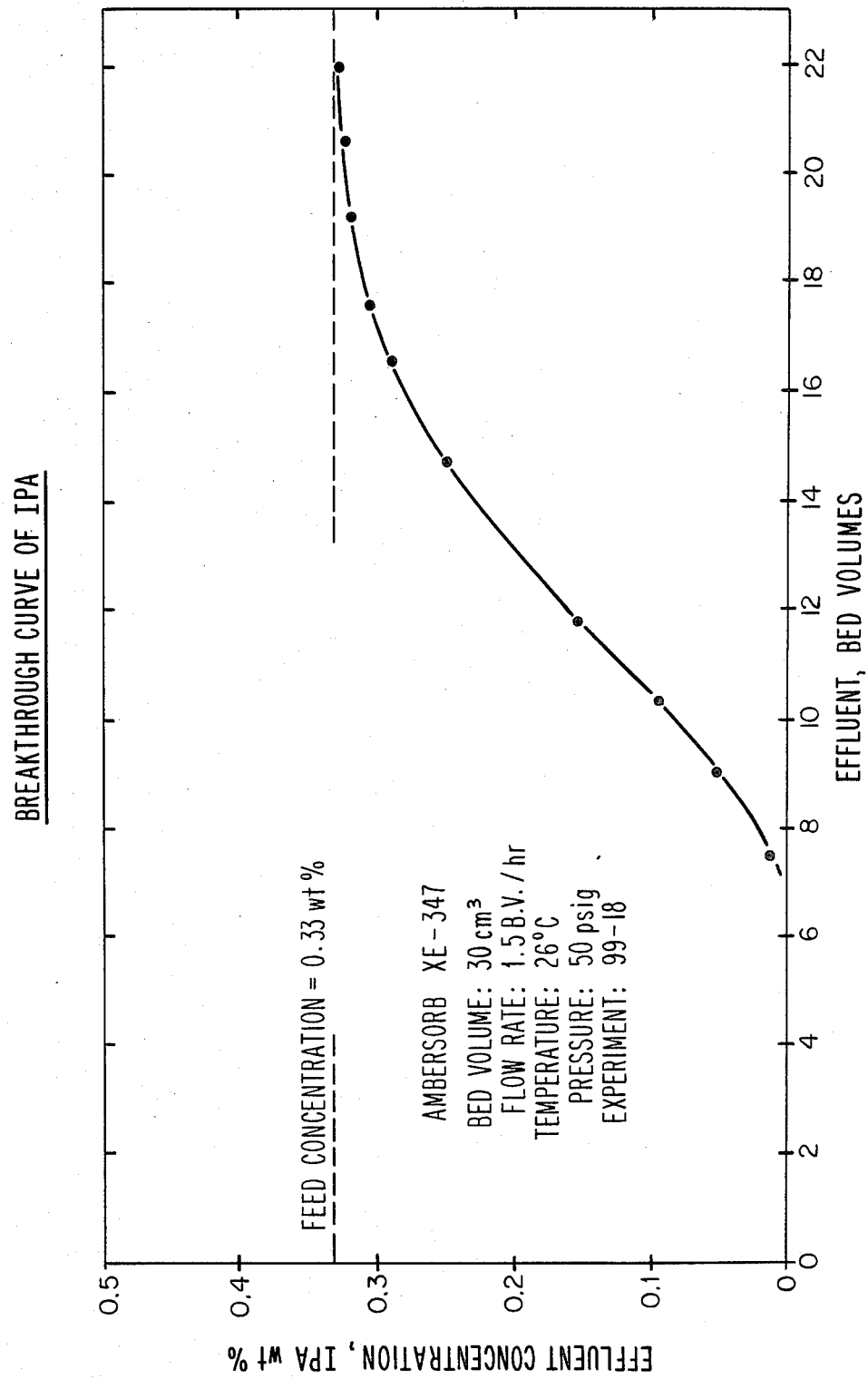
FIG. 3 is a breakthrough curve of isopropyl alcohol on a carbonaceous adsorbent, Ambersorb ® XE-347.
Figure 4:
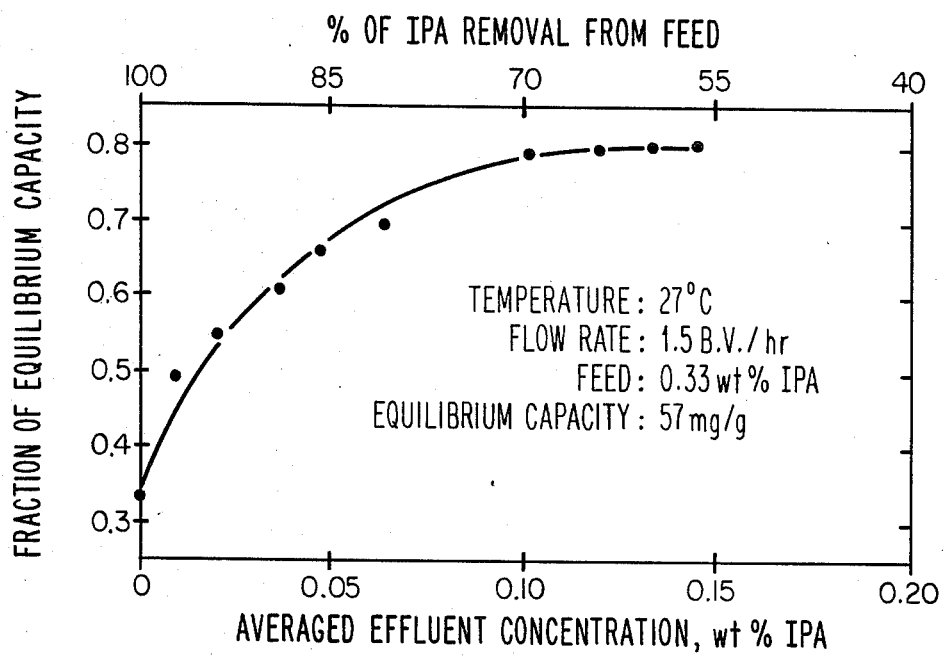
FIG. 4 is a column efficiency versus product purity chart for isopropyl alcohol.
Figure 6:
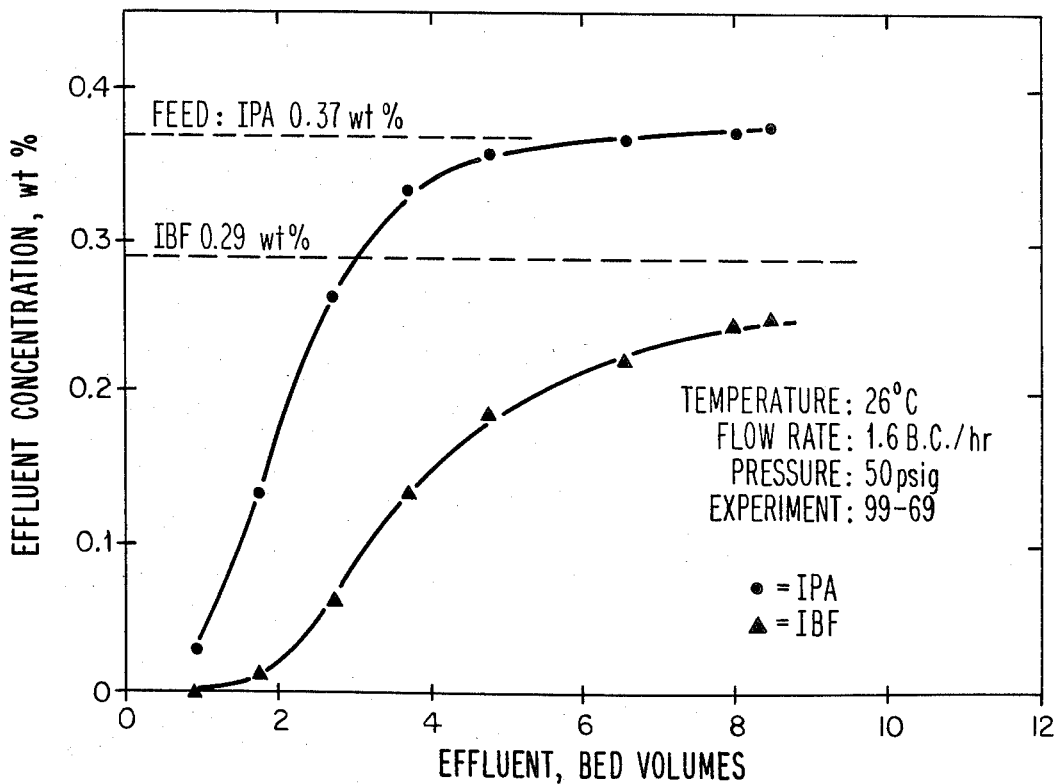
FIG. 6 is a breakthrough curve of IPA and IBF on a tertiary butyl alcohol regenerated Ambersorb ® column.

Using continuous flow column experiments, breakthrough curves for concentrations of IPA were determined, the results of which experiments are illustrated in FIG. 3. Such results were obtained under the same operating conditions for each of the experiments. Essentially, no leakage of IPA occurred for the first 7 bed volumes of effluent at a flowrate of 1.5 bed volumes per hour. After 7 bed volumes, IPA started appearing in the effluent and the feed concentration was slowly approached after 20.2 bed volumes of effluent.

From the foregoing, one of ordinary skill in the art will appreciate that differing percentages of equilibrium capacity may be utilized depending upon the degree of IPA purity desired in the end product. About 33% of the equilibrium capacity of the carbonaceous adsorbent, based on an influent IPA concentration of 0.33 weight percent may be utilized at a space velocity of 1.5 bed volumes per hour to produce approximately 7 bed volumes of IPA-free TBA. As the product purity decreases, i.e., as IPA concentration level in the product increases, the fraction utilization fo the equilibrium capacity or column efficiency increases.

Figure 5A:
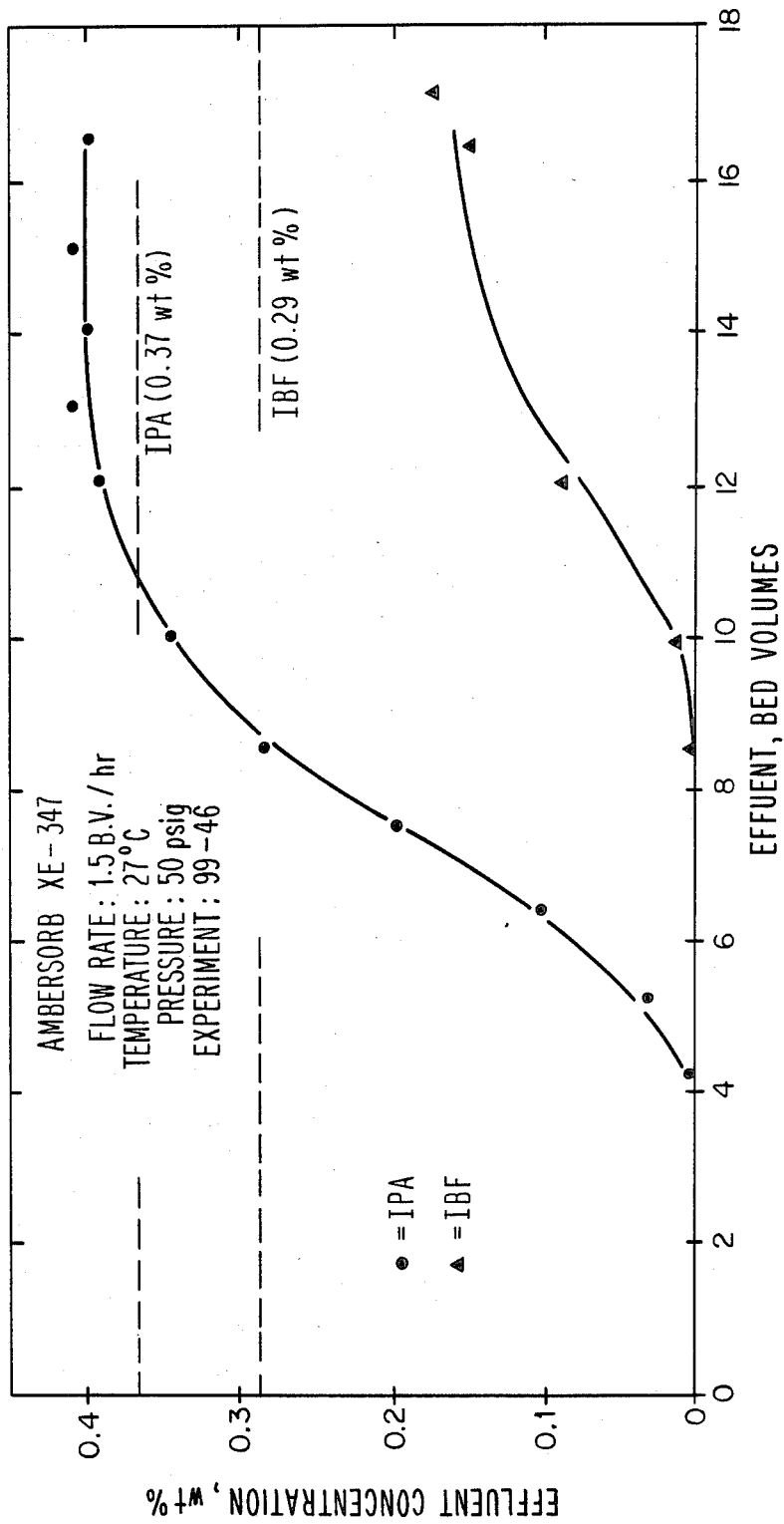
FIG. 5A is a breakthrough curve of isopropyl alcohol and isobutyl formate at 27° C. with a flowrate of 1.5 B.V./hr.
Figure 5B:
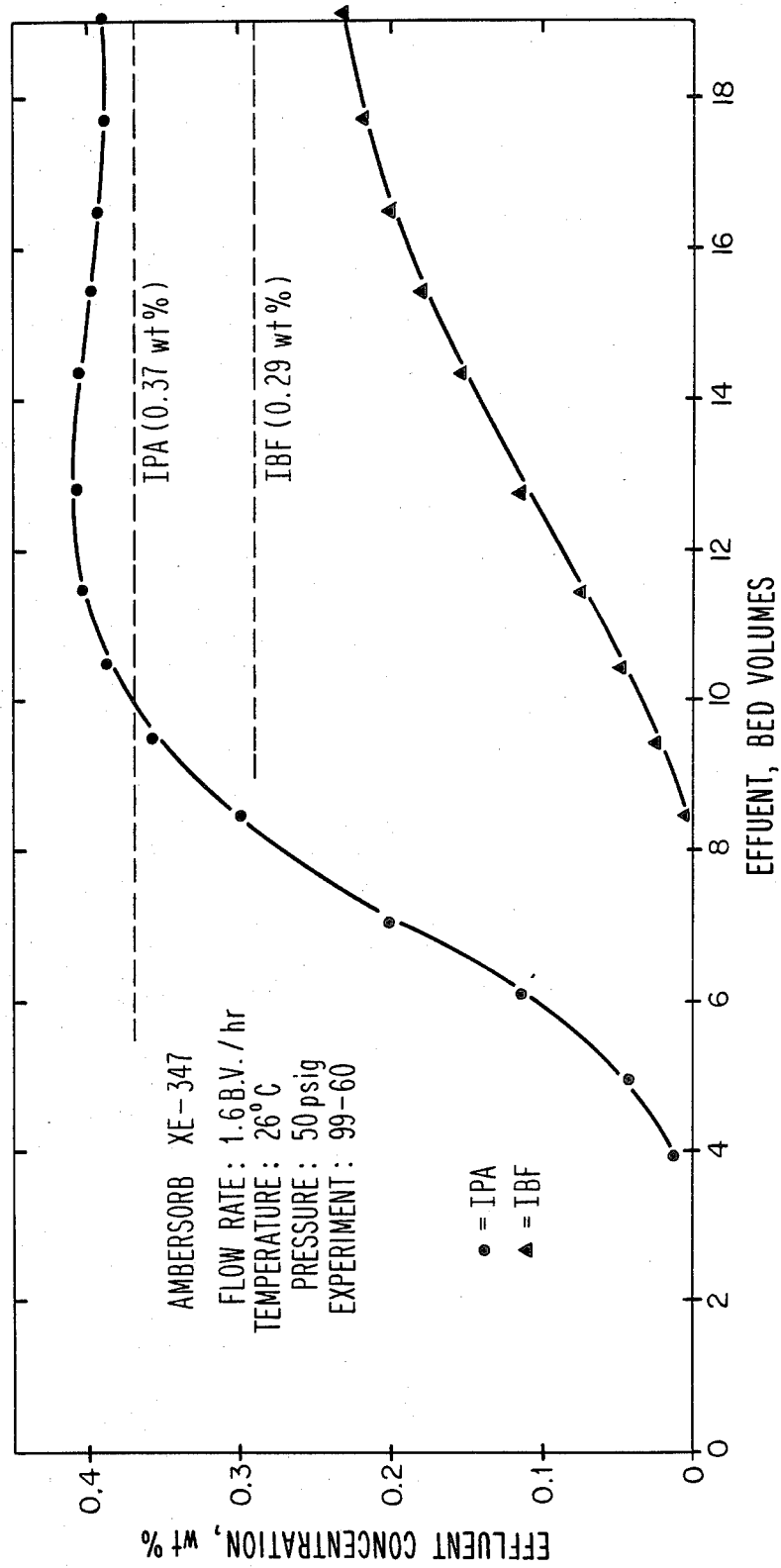
FIG. 5B is a breakthrough curve for isopropyl alcohol and isobutyl formate at 26° C. and a flowrate of 1.6 B.V./hr.

The effect of IBF in the feed on the adsorbtion breakthrough curve of IPA is illustrated in FIGS. 5A and 5B. As illustrated in FIGS. 5A and 5B, IPA concentration breakthrough occurred before IBF concentration breakthrough, indicating that the carbonaceous resin has a higher capacity for IBF than IPA. While the adsorption capacity of IPA decreased due the presence of IBF, the reduction of IPA capacity under these conditions is not as severe as in the case of equilibrium capacity. At IPA breakthrough, about 20% reduction in capacity was observed due to the presence of IBF.

Since pressure was found to have an effect on adsorption capacities only in experiments where fresh adsorbent was used, it is preferred to wet adsorbent particles prior to performing the process of the present invention. Additionally, one of ordinary skill in the art will appreciate that at higher flow rates, inefficiencies in the adsorption process will be experienced. At higher flow rates, time is not adequate to provide sufficient mass transfer of solutes from the bulk of liquid into the micropores. A flowrate of 1.5 bed volumes per hour for adsorption is accordingly preferred.

One of ordinary skill in the art will recognize that it is desirable to be able to regenerate a carbonaceous adsorbent, and that a number of methods may be suitable for regenerating an IPA-saturated adsorbent. It is presently preferred to regenerate the preferred carbonaceous adsorbent with methanol. It has been found, for example, that approximately 95% of the IPA adsorbed on the carbonaceous adsorbent (Ambersorb XE-347) can be removed with 3.5 bed volumes of methanol at ambient temperatures. Variations in temperature and flow rate do not show significant effects on the regeneration efficiency of this process. The removal of IBF from the preferred carbonaceous adsorbent is less efficient than that of IPA from the adsorbent. Once regeneration is complete, effluents of a loading cycle on regenerated adsorbents contained amounts of methanol, as high as 6%, in the first bed volume of effluent. In a commercial installation, it will thus be preferred to provide a product distillation to remove methanol from TBA. Although less preferred at the present time, it is anticipated that a hot TBA stream may be used to partially remove IPA from the spent adsorbent and to restore a fraction of its capacity. Experiments have indicated that about 60% IPA and 20% IBF can be removed from XE-347 adsorbents using 3 bed volumes of TBA at 60° C. Temperatures below the boiling point of TBA are preferred for such regenerations. At the present time, thermal regeneration of spent carbonaceous adsorbent is not preferred.

Alternatively, it is anticipated that hot $N_2$ or $CH_4$ gas may be used to regenerate the adsorbent.

In any commercial process requiring regeneration of an adsorbent, it is important to determine the life of the adsorbent. Using accelerated conditions at flowrates of 3 bed volumes and 1.5 bed volumes per hour for adsorption and methanol regeneration, respectively, after a total of 143 adsorption/methanol regeneration cycles, Ambersorb ® XE-347 adsorbent appears to have no change in physical properties. The adsorption capacity of Ambersorb ® approaches a steady state constant value after a break-in period which remains reasonably constant throughout the test. Accordingly, it is not believed that significant irreversible accumulations of IPA or IPF occur in the adsorbent.

In accordance with the preferred embodiment of the present invention, an IPA-containing process stream may be treated with a plurality of adsorption units/stages which may be placed on line selectively. By using multiple stages, it should be possible to perform a continuous process by taking a proportion of the adsorbers off-line at any given time for regeneration. This removal may be triggered by the detection of a preselected concentration breakthrough, which will indicate that regeneration of a given adsorber is necessary. In the case where methanol regeneration is to be effected as mentioned above a final purification column should be provided whereby methanol is removed as a distillate, the high purity TBA being removed as a bottoms product.

The present invention may further be understood by reference to the following examples:

EXAMPLE 1

Thirteen grams of Ambersorb ® XE-347 are placed in a 1.09 centimeter inner diameter 316 stainless steel column. The bed depth is 22 centimeters. A synthetic liquid stream containing 1.67 wt% isopropyl alcohol (IPA) in tert-butyl alcohol is passed through the column at a volumetric flow rate of 46 cc/hr. This experiment is conducted at ambient temperature and atmospheric pressure. Discrete effluent samples are collected manually at predetermined intervals. Effluent samples are analyzed for isopropyl alcohol concentration by a gas chromatograph. The results are shown in Table III.

TABLE III

Selective Adsorption of IPA on Ambersorb ® XE-347

| Elapsed Time (minutes) | Leakage (wt % IPA) |
|---|---|
| 0 | 0 |
| 15 | 0 |
| 35 | 0.027 |
| 55 | 0.28 |
| 75 | 0.57 |
| 95 | 0.90 |
| 115 | 1.12 |
| 175 | 1.48 |
| 210 | 1.55 |
| 260 | 1.58 |

EXAMPLE 2

Seventeen grams of Molecular Sieve 5A (manufactured by Grace, Davison Division) are placed in a 1.09 centimeter inner diameter 316 stainless steel column. The bed depth is 27 centimeters. A synthetic liquid stream containing 0.35 wt% of isopropyl alcohol in tert-butyl alcohol is passed through the column at a volumetric flow rate of 14 cc/hr at ambient temperature and atmospheric pressure. Effluent samples were collected and analyzed. The results are shown in Table IV.

TABLE IV

Selective Adsorption of IPA on Davison's 5A Molecular Sieve

| Elapsed Time (minutes) | Leakage (wt % IPA) |
|---|---|
| 0 | 0 |
| 45 | 0 |
| 75 | 0.10 |
| 135 | 0.18 |
| 195 | 0.23 |
| 260 | 0.26 |
| 326 | 0.27 |
| 388 | 0.27 |
| 448 | 0.27 |
| 509 | 0.29 |
| 577 | 0.29 |
| 607 | 0.29 |

EXAMPLE 3

Twenty-one grams of Ambersorb ® XE-347 are placed in a 1.09 centimeter inner diameter 316 stainless steel column. The bed deth is 32 centimeters. A synthetic liquid stream containing 0.33 wt% isopropyl alcohol in tert-butyl alcohol is passed through the column at a volumetric flow rate of 42 cc/hr. This experiment is conducted at ambient temperature and a pressure of 50 psig. The results are shown in Table V.

TABLE V

Selective Adsorption of IPA or Ambersorb ® XE-347

| Elapsed Time (minutes) | Leakage (wt % IPA) |
|---|---|
| 0 | 0 |
| 20 | 0 |
| 80 | 0 |
| 140 | 0 |
| 200 | 0 |
| 260 | 0 |
| 320 | 0.015 |
| 380 | 0.046 |
| 440 | 0.096 |
| 500 | 0.101 |
| 560 | 0.123 |
| 620 | 0.226 |
| 696 | 0.286 |
| 740 | 0.307 |
| 802 | 0.318 |
| 862 | 0.323 |
| 932 | 0.325 |

EXAMPLE 4

Eighteen grams of Ambersorb ® XE-347 are placed in a 1.09 centimeter inner diameter 316 stainless steel column. The bed depth is 27 centimeters. A plant stream containing 0.432 wt% isopropyl alcohol and 0.09 wt% isobutyl formate in tert-butyl alcohol is passed through the column at a volumetric flow rate of 46 cc/hr. This experiment is conducted at ambient temperature and atmospheric pressure. The results are shown in Table VI.

TABLE VI

Selective Adsorption of IPA from Plant Stream on Ambersorb ® XE-347

| Elapsed Time (minutes) | Leakage wt % IPA | wt % IBF |
|---|---|---|
| 0 | 0 | 0 |
| 21 | 0 | 0 |
| 45 | 0 | 0 |
| 65 | 0 | 0 |
| 95 | 0 | 0 |
| 128 | 0.012 | 0 |
| 160 | 0.045 | 0 |
| 195 | 0.097 | 0 |
| 232 | 0.177 | 0 |
| 282 | 0.265 | 0 |
| 337 | 0.339 | 0 |
| 407 | 0.388 | 0 |
| 448 | 0.416 | 0 |
| 482 | 0.438 | 0 |

EXAMPLE 5

Spent Ambersorb ® XE-347 adsorbent in Example 3 is eluted with methanol at a volumetric flow rate of 30 cc/hr. This experiment is conducted at 44° C. and atmospheric pressure. All IPA previously adsorbed is removed from the adsorbent. The results are shown in Table VII.

TABLE VII

Desorption Of IPA from Ambersorb ® XE-347 With Methanol

| Elapsed Time (minutes) | Effluent Concentration wt % IPA |
|---|---|
| 0 | 0 |
| 35 | 0.372 |
| 60 | 5.754 |
| 103 | 2.550 |
| 133 | 0.336 |
| 163 | 0.132 |
| 193 | 0.071 |
| 223 | 0.043 |
| 253 | 0.01 |
| 310 | 0 |
| 340 | 0 |

EXAMPLE 6

Spent Ambersorb ® XE-347 adsorbent in Example 4 is eluted with methanol at a volumetric flow rate of 35 cc/hr at ambient temperature and atmospheric pressure. All IPA and about 90% IBF are removed from the adsorbent. The results are shown in Table VIII.

TABLE VIII

Desorption Of IPA And IBF From Spent Adsorbent With Methanol

| Elapsed Time (minutes) | Effluent Concentration wt % IPA | wt % IBF |
|---|---|---|
| 0 | 0 | 0 |
| 30 | 0.59 | 0.33 |
| 60 | 1.39 | 1.74 |
| 100 | 0.12 | 0.36 |
| 140 | 0.05 | 0.11 |
| 180 | 0 | 0.04 |
| 220 | 0 | 0.01 |

While the terms "adsorbent" and "pores" have been used in connection with the foregoing description, one of ordinary skill in the art will recognize that "sieves", "filters", "zeolite materials", etc. may eventually be developed which are capable of performing the method of the present invention, and that such materials may have "pores", "openings" or "voids" defined therein of the sizes disclosed and claimed herein which will be suitable for practicing the methods of this invention. One of ordinary skill in this art will also recognize from the foregoing description that the pores of the preferred adsorbent may have lengths substantially in excess of 5 angstroms, and that, provided the proper widths are maintained, selectivity will nonetheless be maintained. Similarly, the minimum width of such pores should in all instances be no less than, and preferably just slightly greater than the minimum diameter of an IPA molecule. Such widths are thus preferably less than five angstroms and greater than about three angstroms.

As seen from the above, the process of the present invention provides a simple, cost effective method for removing IPA from a TBA process stream, which removal is made possible through the provision of an adsorbent having asymetric pores exhibiting a high selectivity for IPA.

What is claimed is:

1. A method for purifying a process stream of tertiary butyl alcohol containing isopropyl alcohol comprising the steps of:
   (a) providing a macroporous carbon molecular sieve adsorbent having asymetric pores of lengths greater than 5 angstroms and widths of less than five and greater than about 3 angstroms, said adsorbent being characterized as having a bimodal distribution of pore sizes, about half of the pore volume consisting of transport pores of 100–300 angstroms in diameter and the remainder being slit-shaped openings four to six angstroms wide;
   (b) contacting said adsorbent with said process stream to selectively adsorb isopropyl alcohol from said process stream.

* * * * *